(12) United States Patent
Anapliotis

(10) Patent No.: US 6,514,224 B1
(45) Date of Patent: Feb. 4, 2003

(54) DEVICE FOR TAKING A BIOLOGICAL OR CYTOLOGICAL SMEAR

(75) Inventor: Emmanuel Anapliotis, Berlin (DE)

(73) Assignee: Merete Management GmbH, Berlin (DE)

( * ) Notice: Subject to any disclaimer, the term of this patent is extended or adjusted under 35 U.S.C. 154(b) by 0 days.

(21) Appl. No.: 09/869,665

(22) PCT Filed: Jan. 4, 2000

(86) PCT No.: PCT/EP00/00018

§ 371 (c)(1),
(2), (4) Date: Jun. 29, 2001

(87) PCT Pub. No.: WO00/40157

PCT Pub. Date: Jul. 13, 2000

(30) Foreign Application Priority Data

Jan. 4, 1999 (DE) .......................... 199 00 683

(51) Int. Cl.[7] ..................... A61M 35/00; A61F 13/20; B65D 81/24
(52) U.S. Cl. ................. 604/1; 604/15; 604/16; 604/17; 604/18; 206/209; 206/210
(58) Field of Search ................. 604/1, 15, 16, 604/17, 18; 206/209, 210

(56) References Cited

U.S. PATENT DOCUMENTS

| | | | | | |
|---|---|---|---|---|---|
| 2,839,049 | A | * | 6/1958 | MacLean | 600/569 |
| 4,485,824 | A | * | 12/1984 | Koll | 435/304.1 |
| 4,586,604 | A | * | 5/1986 | Alter | 206/209 |
| 4,749,655 | A | * | 6/1988 | Monthony et al. | 600/572 |
| 5,000,193 | A | * | 3/1991 | Heelis et al. | 600/573 |
| 5,163,441 | A | * | 11/1992 | Monthony et al. | 435/287.2 |
| 5,201,323 | A | * | 4/1993 | Vermeulen | 600/569 |
| 5,217,023 | A | * | 6/1993 | Langdon | 600/569 |
| 5,295,952 | A | * | 3/1994 | Pietrafitta | 604/1 |
| 5,339,828 | A | * | 8/1994 | Keating et al. | 600/562 |
| 5,456,265 | A | * | 10/1995 | Yim | 600/569 |
| 5,522,795 | A | * | 6/1996 | Green et al. | 604/1 |
| 6,248,294 | B1 | * | 6/2001 | Nason | 422/100 |

FOREIGN PATENT DOCUMENTS

| | | |
|---|---|---|
| DE | 297 19 659 U1 | 2/1998 |
| EP | 0 031 228 A1 | 7/1981 |

* cited by examiner

Primary Examiner—William C. Doerrler
Assistant Examiner—Filip Zec
(74) Attorney, Agent, or Firm—Hahn Loeser + Parks LLP; Stephen L. Grant

(57) ABSTRACT

A device for taking a sample from the human or animal body comprising a casing tube (2) in which there is longitudinally movably arranged a swab carrier (1) whose distal end is provided with a swab (4), and a displacement device (3) which is arranged at the proximal end of the device and by the actuation of which the swab (4) can be extended from the casing tube (2) or completely retracted thereinto, wherein the swab carrier (1) comprises at least a distal carrier portion (10) and a tubular proximal carrier portion (11), which are releasably connected together by way of a coupling portion (12) which is introduced into the proximal carrier portion (11) and which extends in the distal direction into a first opening (13) at the proximal end of the distal carrier portion (10), and wherein the coupling portion (12) locks the carrier portions relative to each in their longitudinal direction in such a way that the connection thereof is releasable by pulling the distal end of the coupling portion (12) in the proximal direction out of the opening (13).

32 Claims, 4 Drawing Sheets

DEVICE FOR TAKING A BIOLOGICAL OR CYTOLOGICAL SMEAR

The invention concerns a device as set forth in the classifying portion of claim 1.

BACKGROUND OF THE ART

Numerous inflammations in the human or animal urogenital tract are to be attributed to a large number of widely varying germs or microbes. Thus for example the etiology of Fallopian tube inflammation (salpingitis) is polymicrobial. Aerobic and anaerobic germs, mycoplasmas and chlamydiae can be identified in that respect. That identification can be achieved on the one hand from the Douglas fluid surrounding the Fallopian tubes or by smears from the Fallopian tubes. Particularly for intracellularly growing chlamydiae proof based on cell-rich examination material has proven to be an indispensable prerequisite as the Douglas fluid has a low cell content and in addition has an anti-microbial effect. For that reason the smear is also to be preferred for other bacteria identification procedures.

A number of devices of the general kind indicated is known for taking biological or cytological smears of that kind. Such devices are generally usable a plurality of times insofar as a fresh swab is fixed on the swab carrier for each new smear. To take a smear on the Fallopian tube the devices are generally moved to the Fallopian tube through a trocar. For smears at other locations which are more readily accessible in the urogenital tract the use of a trocar however may possibly be unnecessary.

Thus for example U.S. Pat. No. 5,295,952 discloses such a device in which the two carrier portions are connected together by way of a positively locking connection which locks in the longitudinal direction of the swab carrier. Locking transversely with respect to the longitudinal direction of the swab carrier is effected by way of a tubular coupling portion which is fitted over the two carrier portions.

The known devices however suffer from a large number of disadvantages. Thus on the one hand they are distinguished by virtue of being of a relatively complicated structure which is susceptible to trouble. Thus for example securely and releasably fixing the swabs on the swab carrier can be achieved, not only having regard to the tightly constricted spatial conditions, only with a very high degree of structural complication and expenditure which on the one hand has an adverse effect on the manufacturing costs of the individual components.

In addition, this design configuration also involves the disadvantage that the swab has to be released from the swab carrier after the smear has been taken. That operation of releasing the swab from the swab carrier is generally possible however only by means of suitable aids or tools, the use of which however under some circumstances can entail contamination of the swab. Contamination of that kind however, even in a very small amount, can seriously falsify the examination result.

The swab with the smear generally has to be initially stored in a transportation fluid for subsequent evaluation in the laboratory. Depending on the respective duration of the period of time between the operation of taking the sample and evaluation thereof, even very slight contamination can result in damage to or impairment of the smear on the swab or however also the transportation fluid and can thus result in falsification of the examination result.

A further disadvantage lies in the relatively expensive and complicated cleaning and sterilization of the multiply re-usable components of the known devices. Contamination which is not removed, precisely at locations which involve difficulties of access within the mechanism of the devices and the thermally or chemically induced component stresses which occur in the cleaning and sterilization procedure can also have an adverse effect on the susceptibility to trouble of the devices.

SUMMARY OF THE INVENTION

The object of the invention is therefore that of providing a device of the kind set forth in the opening part of this specification, which is simple and inexpensive to produce and which does not suffer from the above-indicated disadvantages or which involves them only to a lesser degree and which in particular ensures examination results which are as unfalsified as possible.

Based on a device as set forth in the classifying portion of claim 1, that object is attained by the features recited in the characterizing portion of claim 1.

The invention entails the technical teaching that a device which is particularly simple and inexpensive to produce and which is reliable in operation and which ensures examination results which are as unfalsified as possible is achieved if the swab carrier comprises at least a distal carrier portion and a tubular proximal carrier portion, which are releasably connected together by way of a coupling portion which is introduced into the proximal carrier portion and which to release the connection between the two carrier portions is pulled in the proximal direction out of its seat in the distal carrier portion.

In that arrangement the coupling portion extends in a distal direction into a first axial opening at the proximal end of the distal carrier portion and locks the carrier portions relative to each in their longitudinal direction in such a way that the connection thereof is releasable by pulling the distal end of the coupling portion in the proximal direction out of the first axial opening. In that arrangement the coupling portion still extends in the proximal direction through the actuating grip so that it can be gripped at its proximal end and can be pulled in the proximal direction out of its seat in the distal carrier portion.

It will be appreciated that the movement of pulling the coupling portion out in the proximal direction does not have to involve a pure translatory movement. It is likewise possible for a translatory movement to be combined with a rotational movement about the longitudinal axis of the coupling portion, for that purpose. That may be desired or even necessary in particular when the coupling portion is locked in position in positively locking relationship.

By virtue of the connection between the carrier portions being simple to release, the distal carrier portion with the swab disposed thereon can be detached, after the smear has been taken, without that involving touching those regions which are to be separated from each other, possibly by means of special tools or the like, which could result in contamination. The distal carrier portion which is to be removed, with the swab carrying the smear, only has to be positioned over or introduced into the opening of the transportation vessel filled with the transportation fluid. The coupling portion is then gripped at its proximal end and pulled relative to the swap carrier in the proximal direction until it is released from its seat in the first opening in the distal carrier portion. In that way the distal carrier portion is released from the proximal carrier portion and can slide into the transportation vessel filled with transportation fluid, without coming into contact with other objects when that happens.

The operation of removing the distal carrier portion with the swab can be carried out quickly and in an uncomplicated fashion in no time at all. The removal operation can be carried out in any longitudinal position of the swab carrier. Preferably however it is effected in the first longitudinal position of the swab carrier as the swab with the smear is then disposed in the interior of the casing tube and is thus substantially protected from unintended contamination.

Preferably that longitudinal position is characterized by a resistance which is perceptible for the operator when actuating the displacement device. Further preferably that resistance is afforded by an end abutment which is provided in the displacement device or between the casing tube and the swab carrier and beyond which no further actuation of the displacement device is possible.

The swab carrier is preferably in the form of a one-trip or disposable portion. That ensures that the device is of a particularly simple structure which is inexpensive to produce and which operates reliably, as for example no fixing devices which are of a complicated structure and which are to be used a plurality of times are required for the swab and the carrier portions respectively.

Preferably the entire device is designed for single use. It will be appreciated that this eliminates the expensive procedure for cleaning and sterilizing the device after the smear has been taken. It is however also possible for only the distal carrier portion with the swab and possibly also the casing tube or parts thereof to be constructed as one-trip or disposable components, while the rest of the device with the displacement device is designed for multiple use.

In preferred embodiments of the device according to the invention the coupling portion has at least one distal locking part and at least one proximal locking part. In that arrangement the distal locking part co-operates lockingly and releasably in the distal direction with a first wall part of the distal carrier portion. The proximal locking part co-operates lockingly and also releasably in the proximal direction with a second wall part of the proximal carrier portion or the actuating grip. As a result, the distal carrier portion is locked in the distal direction and the proximal carrier portion or the actuating grip connected thereto is locked in the proximal direction, to the coupling portion, whereby the two mutually adjoining carrier portions are fixed relative to each in a simple fashion.

The releasable connection between the respective locking part and the respective carrier portion can be designed in known manner in the form of a releasable positively locking connection. For that purpose for example one or more detent elements which are resilient transversely with respect to the longitudinal direction and which are respectively arranged on the one component can engage into corresponding undercut configurations in the other component. In that case, the resilient detent elements can be arranged both on the coupling portion and also on the respective carrier portion or the actuating grip.

Preferably, the connection between the distal locking part and the distal carrier portion or the connection between the proximal locking part and the proximal carrier portion or the actuating grip can be designed in the manner of a frictional locking connection which is releasable in the axial direction of the coupling portion.

It will be appreciated however that, in other variants of the device, for the respective connection between the carrier portion and the coupling portion, it is also possible to select a combination of a positively locking connection and a frictional locking connection for the respective connection, or one of the connection can be formed by a frictional locking connection and one of the connections can be formed by a positively locking connection. It will be appreciated also that the two connections can be made or afforded in different ways.

The preferred variant with the frictional locking connections is distinguished in that the first and second wall parts can be of a particularly simple nature, in particular without undercut configurations or the like. That considerably reduces the manufacturing expenditure for the two carrier portions. Thus in the situation which is easiest to manufacture the wall parts in question are of a substantially cylindrical configuration.

Preferably in that arrangement to provide the releasable frictional locking connection the respective locking part is of an oversize, at least in a portion-wise manner, transversely with respect to its longitudinal direction, in relation to the first and second wall part respectively. Depending on the respective elasticity of the components to be paired, the oversize is such that on the one hand a sufficiently firm fit of the coupling portion in the respective component and thus sufficiently reliable locking of the carrier portions relative to each is guaranteed. On the other hand the oversize is such that the distal end of the coupling portion can still be pulled with the application of a reasonable amount of force out of its seat in the first opening in the distal carrier portion.

In other variants the oversize and thus the frictional engaging pairing is achieved by one or more spring elements which are resilient transversely with respect to the longitudinal direction and which are respectively arranged on the one component and which press by virtue of their biasing effect transversely with respect to the longitudinal direction against corresponding friction surfaces on the component coupled thereto. The biasing effect with which the spring elements bear against the friction surfaces of the other component and therewith also the locking threshold or release force achieved can be relatively accurately determined by the dimensioning of the spring elements without in that respect having to observe particularly close dimensional tolerances. That reduces the manufacturing expenditure for the components in question.

In this case the spring elements can form at least a portion of the respective first and second wall parts respectively. The spring elements can be arranged in other words on the respective carrier portion. Variants of the device according to the invention, which are particularly simple to produce, are however distinguished in that the distal or proximal locking part is of a resilient nature transversely with respect to its longitudinal direction and bears with a biasing effect against the respective wall part.

In a development of the invention which is desirable because it can be produced at low cost the first and second wall parts are of a substantially cylindrical configuration and the respective locking part is formed by a spiral-shaped part. In that case the spiral-shaped part is preferably formed by a suitably wound metal wire.

In further preferred developments of the device according to the invention the proximal carrier portion, at its distal end, for receiving the distal end of the coupling portion which is drawn out of the first axial opening, is of inside dimensions which substantially correspond to the inside dimensions of the first axial opening. That ensures that, when the coupling portion is pulled out of its seat in the first opening, a substantially constant pulling force is to be applied to the coupling portion, during the entire release operation. That avoids jerky movements which can arise when pulling out the coupling portion as a consequence of a reduction in the pulling force required for pulling out the coupling portion, which was not expected by the operator. That makes it easier to introduce the detached distal carrier portion with the swab carrying the smear, into the transportation container.

It will be appreciated however that, in other variants of the invention, a drop in the pulling force to be applied can be achieved by the proximal carrier portion at its distal end for example being of an inside dimension which is sufficiently great for receiving, substantially free of resistance, the distal end of the coupling portion, which end is pulled out of the first axial opening. Likewise by virtue of a suitable configuration of the coupling portion and the proximal carrier portion, it is possible to produce a rise in the force required for pulling out the coupling portion as soon as the coupling portion is released from the distal carrier portion in order to signal that condition to the operator.

Preferred variants of the device according to the invention are distinguished in that, at its end which projects in the proximal direction out of the actuating grip, the coupling portion has a grip device for pulling its distal end in a proximal direction out of the first axial opening. That permits the distal carrier portion with the swab to be quickly detached, without aids being required.

In accordance with a preferred development of the invention the device has at least one securing means to prevent the distal end of the coupling portion from being unintentionally pulled out of the first opening. The securing means can be designed in many known ways. Thus for example the securing means can comprise a releasable clamping device or the like which is arranged at the proximal end of the actuating grip in the exit region of the coupling portion and which fixes the coupling portion relative to the actuating grip and therewith also relative to the carrier portions of the swab carrier.

It is also possible to provide a releasable securing means which acts by positively locking, for example a securing pin or the like, which engages into suitable openings in the coupling portion and in the actuating grip.

Preferably the securing means is such that it is destroyed when the distal end of the coupling portion is pulled out of the first axial opening. For that purpose it may for example comprise an adhesive point consisting of a plastic material which suitably hardens and which is sufficiently firmly joined both to the material of the coupling portion and also the material of the component which in that region adjoins the coupling portion. It is equally also possible for the securing means to be in the form of a plastic diaphragm or the like which is shaped or molded on the coupling portion and which is then clamped fast for example in the seat of the proximal carrier portion in the actuating grip or which is fixed in some other fashion to those components.

These variants are distinguished by the securing means being particularly simple and thus inexpensive to produce. Such a securing means can be disposed at any locations of the coupling portion, for example at the exit of the coupling portion from the actuating grip, but also at the distal end of the proximal carrier portion or even in the first opening of the distal carrier portion.

In advantageous variants of the device according to the invention the securing means also forms the means for locking the coupling portion in the distal carrier portion or in the proximal carrier portion or the actuating grip, thereby providing that the device is of a particularly simple structure which is reliable in operation.

In other advantageous variants of the invention, it is provided that the coupling portion and the carrier portions are such that the carrier portions are fixed by the coupling portion transversely with respect to their longitudinal direction in a position of being substantially aligned in their longitudinal direction. That makes it unnecessary to provide corresponding guide means on the carrier portions, which hold the latter in their mutually aligned position.

In a further preferred embodiment of the device according to the invention the difference between the inside dimensions of the casing tube and the outside dimensions of the swab carrier or the swab is such that the end region of the swab carrier which is disposed distally of the first structural weakening is released after separation thereof from the casing tube by virtue of the action of the force of gravity when the casing tube is suitably inclined. That permits particularly simple handling of the sample on the swab, after the smear has been taken. It is sufficient in this case for example for the distal end of the device to be positioned perpendicularly above the opening of the filled transportation vessel and for the distal carrier portion to be removed in the above-described manner. The carrier portion which has been removed and on which is disposed the swab with the smear is then released from the casing tube as a result of the action of the force of gravity, and slides into the transportation fluid. This variant therefore also provides that the component of the device which carries the sample that is to be later analyzed passes into the transportation vessel without coming into contact with possible sources of contamination. Preferably, for that purpose, the inside dimensions of the casing tube in the distal end region have a slight oversize relative to the outside dimensions of the distal carrier portion or the swab.

The dimensional difference can however also be such that, in addition to the force of gravity, the action of weak inertia forces, for example due to gentle shaking or the like, also provides for release from the casing tube.

A further advantage of the device according to the invention in this respect is that, in the event of the separated distal carrier portion sticking in the casing tube, the coupling portion can be displaced in the distal direction again in order to release or push the distal carrier portion out of the casing tube.

Preferably the length of the distal carrier portion is substantially at least 1 cm, preferably at least 2 cm, and does not exceed an amount of substantially 10 cm, preferably 5 cm. That ensures simple appropriate transportation in transportation vessels which are in current use at the present time.

In advantageous developments of the invention the swab carrier, the casing tube and the displacement device are so designed that the swab carrier is rotatable about the longitudinal axis at least in its second longitudinal position relative to the casing tube. That ensures that a sufficiently large amount of sample can be easily taken, by the swab being brought into contact with the part of the body to be examined, by rotation about the longitudinal axis of the swab, over preferably its entire periphery. That is effected in accordance with the invention without the casing tube having to be rotated for that purpose. It is precisely in the case of a device which is inserted through a trocar that such rotation of the casing tube, by virtue of the generally relatively firm fit of the casing tube in the jacket tube of the trocar, is relatively difficult or involves the application of an increased amount of force, which once again could result in damage to the device.

The displacement device can be designed in many known ways. It is thus for example possible for the actuating grip to be guided relative to the grip element in known manner by means of a guide pin or the like which is arranged for example on the actuating grip and which engages into a corresponding guide groove extending in the grip element. Then, when the swab carrier is in the second longitudinal position, the guide groove must extend in the peripheral direction of the casing tube or swab carrier so that corresponding rotation of the swab carrier relative to the casing tube is possible.

Preferably in that case the swab carrier is rotatable relative to the casing tube through at least substantially a full revolution in order advantageously to make use of the entire periphery of the swab for taking the sample. It will be appreciated however that certainly satisfactory results can also be achieved with a smaller angle of rotary movement.

In the case of a variant which is particularly advantageous because it is simple to produce the actuating grip includes an advance device and a rotating device which is fixedly connected to the proximal end of the swab carrier. The rotating device and/or the swab carrier is or are arranged on the advance device and is or are rotatable relative thereto about the longitudinal axis. In that case for example the proximal end of the swab carrier can be supported rotatably in the advance device, wherein the swab carrier then projects in the longitudinal direction out of the advance device in the proximal direction. Arranged on the portion which projects out of the advance device there is then the rotating device which for example can be formed by a wheel or the like which is carried on the swab carrier or also only by a suitable grip surface on the swab carrier. Preferably however for reasons of strength the rotating device is supported rotatably on or in the advance device.

In further preferred embodiments of the invention the swab carrier or the casing tube and/or the displacement device are designed in such a way that the longitudinal mobility of the swab carrier relative to the casing tube is limited by a proximal abutment device and a distal abutment device, to a longitudinal movement between its first and second longitudinal positions. That provides that the two extreme positions are made clearly perceptible to the operator in a particularly simple and reliable fashion.

In this case, to form the proximal abutment device, a first abutment surface can be provided on the casing tube and a second abutment surface arranged in distal relationship therewith can be provided on the swab carrier or on the actuating grip. To form the distal abutment device, a third abutment surface is then also provided on the casing tube and provided on the swab carrier or on the actuating grip is a fourth abutment surface arranged in proximal relationship therewith. In that case, the second abutment surface, when the first longitudinal position of the swab carrier is reached, bears in a first contact region at least in part against the first abutment surface which is in proximal relationship therewith. In the opposite direction, the fourth abutment surface, when the second longitudinal position of the swab carrier is reached, bears in a second contact region at least in part against the third abutment surface which is in distal relationship therewith. The lines normal to the first and second abutment surfaces respectively extend over the first and second contact regions respectively in parallel relationship with the longitudinal direction. That configuration, by virtue of the orientation thereof, provides first and second abutment surfaces which can be produced in a simple fashion and which reliably limit the longitudinal movement of the swab carrier relative to the casing tube. In this case, the second and fourth abutment surfaces can be of any desired shape, whereby the production thereof can also be a very simple matter.

Preferably but not necessarily the first abutment surface is disposed in proximal relationship with the third abutment surface, as that then permits a particularly simple arrangement of the second and fourth abutment surfaces.

To provide the abutment devices, the arrangement may have a projection which extends radially with respect to the longitudinal axis and which is of a pin-like or nose-like configuration and which engages into a groove extending substantially in the longitudinal direction of the device. In that case the projection is provided at the inside periphery of the casing tube and the groove is then provided in the swab carrier. When the first longitudinal position of the swab carrier is reached the projection then bears against the distal end surface of the groove and when the second longitudinal position of the swab carrier is reached it bears against the proximal end surface of the groove.

Alternatively, the projection is provided at the outside periphery of the swab carrier and the groove extends on the inside of the casing tube. When the first longitudinal position of the swab carrier is reached the projection then bears against the proximal end surface of the groove and when the second longitudinal position of the swab carrier is reached it bears against the distal end surface of the groove.

Both variants are distinguished by being particularly simple to manufacture and by virtue of their operative principle which is reliable in operation because it is a simple mechanical principle.

Preferably, the casing tube and the swab carrier are adapted to be rotatable relative to each about the longitudinal axis, wherein the groove, for locking of the swab carrier in its first and/or second longitudinal position, is designed in the manner of a bayonet locking means at its proximal end and/or its distal end. That provides in a particularly desirable fashion for locking of the swab carrier relative to the casing tube, thereby ensuring simple and reliable handling of the device.

In other advantageous configurations of the device according to the invention the displacement device is designed in the manner of a screw drive which produces an advance movement in the longitudinal direction of the device, thereby affording a displacement mechanism which acts in a particularly simple and reliable fashion. Preferably in that case the casing tube and the swab carrier are adapted to be rotatable relative to each about the longitudinal axis. The displacement device includes a first screwthread which is arranged on the casing tube and which, for producing a longitudinal movement of the swab carrier relative to the casing tube, upon rotation of the actuating grip relative to the casing tube about the longitudinal axis, co-operates with a second screwthread provided on the swab carrier or on the actuating grip, and thus produces a longitudinal movement of the swab carrier relative to the casing tube.

This variant is distinguished by variability, which is particularly high together with ease of manufacture, in terms of the displacement parameters. Thus, it is readily possible to set the advance movement of the swab carrier relative to the casing tube, which is produced per revolution of the actuating grip, by a suitable choice of the screwthread pitch. In addition, multi-flight screwthreads can be provided to enhance the level of operating reliability.

There are a large number of different options in regard to the arrangement of the screwthreads. Thus, the first screwthread can be arranged in the form of a female screwthread on the casing tube while in that case, as will be readily appreciated, the second screwthread must be in the form of a male screwthread for example on the swab carrier.

Preferably however the first screwthread is arranged at the outside periphery of the proximal end of the casing tube and the actuating grip is designed in the manner of a screw cap, in which case the swab carrier is passed through an orifice in coaxial relationship therewith at the distal end of the actuating grip and the second screwthread is arranged at the distal end of the actuating grip at the inside periphery of the orifice. That then affords a robust arrangement which is particularly simple to produce.

In particularly desirable variants of the invention, the pitch of the first and second screwthreads is so selected that the movement of the swab carrier from its first longitudinal position into its second one or vice-versa is implemented by substantially one revolution of the actuating grip relative to the casing tube. That affords a device which is particularly simple to handle and in which the advance movement of the swab carrier relative to the casing tube can be rapidly implemented by means of a single handling operation, with good and simple controllability. Preferably in that case the first screwthread and the second counterpart screwthread are of a multi-flight nature. That prevents jamming of the screw drive in a simple and thus inexpensive manner, this in turn ensuring noise-free operation of the device.

Preferably the casing tube and the swab carrier each comprise biocompatible plastic material and the coupling portion comprises biocompatible plastic material or biocompatible metal so that the risk of adversely affecting the examination results by damage to the smear or the transportation fluid by the material of the casing tube, swab carrier or coupling portion is minimized. In a further preferred feature the actuating grip is in the form of a plastic body produced by casting or injection blow molding. That permits particularly inexpensive manufacture of the actuating grip in a single working operation. That applies in particular also when the actuating grip is to be provided with a motion screwthread.

The swab preferably comprises calcium alginate or a cotton-aluminum mixture or is formed by a nylon brush as those materials ensure that it is particularly easy to take the smear and they do not involve any falsification, or they entail minimized falsification, of the examination results by virtue of an interaction with the smear or the transportation fluid.

It is also desirable if the outer actuating grip is "non-losably" latched on the inner grip element by virtue of an annular abutment surface being provided on the grip element which is connected to the sleeve, the annular abutment surface interacting with an annular abutment surface when the grip element comes free from the screwthread. That forms a blocking means to prevent the actuating grip from being pulled off the grip portion in the situation where the latter is completely unscrewed from the screwthread.

If the swab carrier is to be removed by means of a pair of tweezers, the tweezers can be packaged with the device, in which case a receiving means for the tweezers in the form of a clamping holder is preferably provided on the casing tube or on the grip portion.

BRIEF DESCRIPTION OF THE DRAWINGS

Other advantageous developments of the invention are characterized in the appendant claims or are set forth in greater detail hereinafter together with the description of the preferred embodiment of the invention with reference to the drawings in which:

DETAILED DESCRIPTION OF THE INVENTION

Figure 1:
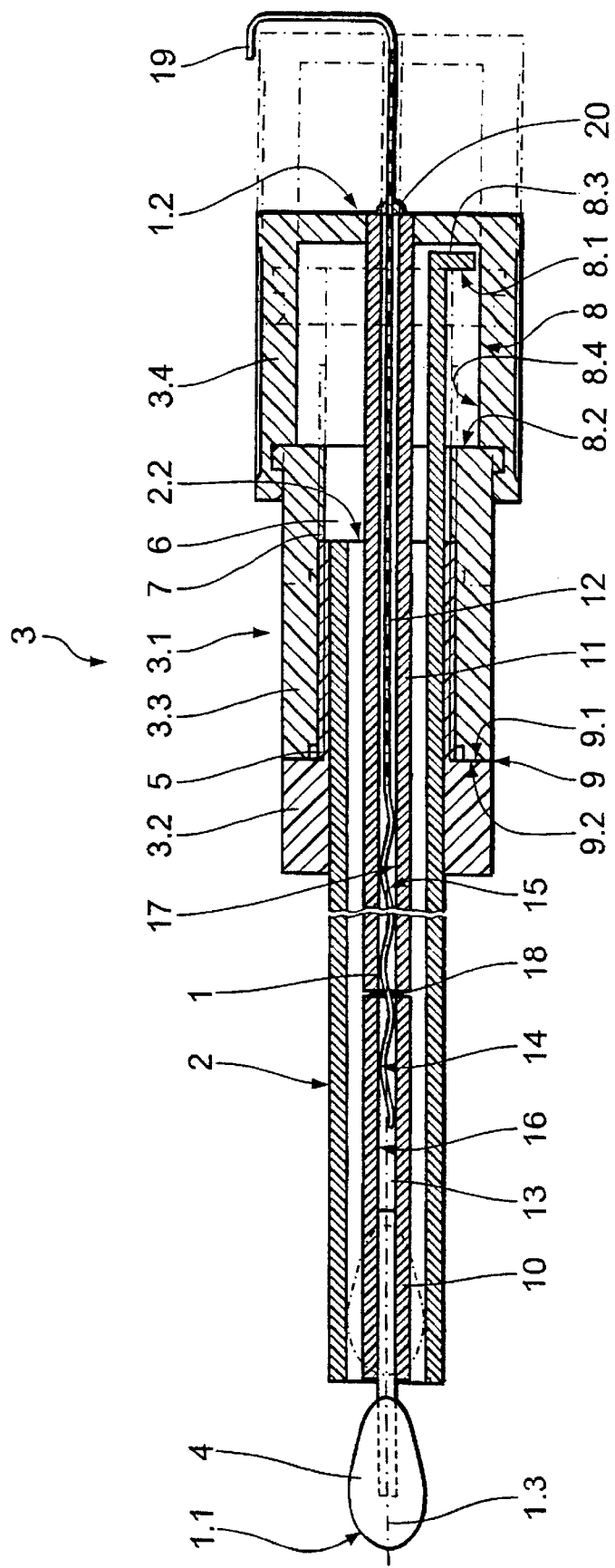
FIG. 1 is a view in section through a preferred embodiment of the device according to the invention.

FIG. 1 shows an embodiment of the device according to the invention comprising a swab carrier 1 which is arranged in a casing tube 2, and a displacement device 3 arranged at the proximal end of the device. The swab 4 is arranged at the distal end 1.1 of the swab carrier 1. The displacement device includes an actuating grip or handle 3.1 fixedly connected to the distal end 1.2 of the swab carrier 1, and a grip element 3.2 which is fixedly arranged on the casing tube 2.

Arranged at the proximal end 2.2 of the casing tube 2 is a first screwthread 5 in the form of a male screwthread on the grip element 3.2. The actuating grip 3.1 is in the manner of a screw cap and includes an advance device 3.3 and a rotating device 3.4 which is arranged freely rotatably relative to the advance device 3.3 about the longitudinal axis 1.3. The actuating grip 3.1 has an orifice 6 which is coaxial with the swab carrier 1 and through which the swab carrier 1 extends. Arranged at the inside periphery of the orifice 6, at the distal end of the advance element 3.3, is a second screwthread 7 which is in the form of a female screwthread and which co-operates with the first screwthread 5 and which forms therewith a screw drive for producing an advance movement in the longitudinal direction of the device of the invention. If consequently the advance element 3.3 of the actuating grip 3.1 is rotated relative to the casing tube 2 about the longitudinal axis 1.3, the swab carrier 1 which is fixedly connected to the rotating element 3.4 of the actuating grip 3.1 performs a longitudinal movement in the direction of the longitudinal axis 3.1, relative to the casing tube 2, in the distal or proximal direction, depending on the respective direction of rotation involved. Depending on whether the rotating element 3.4 is or is not also rotated in that case, the swab carrier 1, besides the longitudinal movement, also performs a rotary movement about the longitudinal axis 1.3.

The longitudinal movement of the swab carrier 1 relative to the casing tube 2 is limited by a proximal abutment device 8 and a distal abutment device 9. In this case the proximal abutment device 8 includes a first abutment surface 8.1 arranged on the casing tube 2 and a second abutment surface 8.2 arranged in distal relationship therewith on the actuating grip 3.1. The distal abutment device 9 has a third abutment surface 9.1 arranged on the casing tube 2 and a fourth abutment surface 9.2 arranged in proximal relationship therewith on the actuating grip 3.1.

The first abutment surface 8.1 is in the form of a flat, distally facing end surface of a component 8.3 formed on the casing tube 2. That component 8.3 extends in the proximal direction from the proximal end 2.2 of the casing tube 2 and is in the form of a barb-like element which is narrow in the peripheral direction. In that case, the part of the component 8.3, which extends parallel to the longitudinal axis 1.3, is of a resilient nature in the radial direction in order to permit easy assembly of the device.

The line normal to the first abutment surface 8.1 extends parallel to the longitudinal axis 1.3 of the device. The second abutment surface 8.2 is formed by the proximally facing distal end surface of an annular groove arranged proximally of the second screwthread 7 in the actuating grip 3.1. In that case, the line normal to the second abutment surface 8.2 also extends parallel to the longitudinal axis 1.3 of the device. The radial spacing of the centerpoint of the first abutment surface 8.1 and the reference circle of the second abutment surface 8.2 and the radial extent of the two abutment surfaces 8.1 and 8.2 approximately correspond to each other so that the first abutment surface 8.1 can bear completely against the second abutment surface 8.2 in order to impede further longitudinal movement of the swab carrier 1 relative to the casing tube 2 in the proximal direction.

The third abutment surface 9.1 is formed on the casing tube 2 in the form of a flat, proximally facing surface of a step provided distally of the first screwthread 5 on the grip element 3.2. The line normal to the third abutment surface 9.1 extends in this case parallel to the longitudinal axis 1.3 of the device. The fourth abutment surface 9.2 is formed by the distal end surface of the actuating grip 3.1. The line normal to the fourth abutment surface 9.2 extends in this arrangement also parallel to the longitudinal axis 1.3 of the device of the invention. The radial spacing of the reference circles and the radial extent of the two abutment surfaces 9.1 and 9.2 approximately correspond to each other so that the third abutment surface 9.1 can bear completely against the fourth abutment surface 9.2 in order to impede further longitudinal movement of the swab carrier 1 relative to the casing tube 2 in the distal direction.

When the actuating grip 3.1 is screwed in the proximal direction relative to the casing tube 2 to such an extent that the first abutment surface 8.1 bears against the second abutment surface 8.2, then the swab carrier 1 is in its first longitudinal position—shown in dash-dotted line in FIG. 1—in which the swab 4 is disposed entirely in the interior of the casing tube 2. In that position, the device is moved to the part of the body at which the smear is to be taken, possibly through the jacket tube of a trocar. The casing tube 2 in that case protects the swab 4 from contamination along the path of insertion thereof to the part of the body to be investigated.

If the actuating grip 3.1 is screwed in the distal direction relative to the casing tube 2 to such an extent that the third abutment surface 9.1 bears against the fourth abutment surface 9.2, the swab carrier 1 is in its second longitudinal position—shown in solid lines in FIG. 1—in which the distal end 1.1 of the swab carrier 1 projects in the distal direction out of the distal end 2.1 of casing tube 2. In this case, in the illustrated embodiment, the swab 4 is disposed completely outside the casing tube 2. In that longitudinal position the swab 4 is brought into contact with the part of the body to be investigated, to receive the smear. In that case, the operator rotates the rotating element 3.4 through at least one revolution relative to the advance element 3.3 of the actuating grip 3.1 and therewith also the swab carrier 1 and the swab 4 relative to the casing tube 2 which is more or less held fast in the jacket tube of the trocar. In that way the swab 4 is easily brought into contact over its entire periphery with the part of the body to be investigated, to pick up the sample. After the smear has been taken by the swab 4 it is moved into its first longitudinal position again by rotation of the advance element 3.3 of the actuating grip 3.1 relative to the casing tube 2, with the swab 4 in the first longitudinal position thereof being protected by the casing tube 2 from contamination as it is brought out of the body.

For the sake of comfortable and ergonomic handling of the device the grip device 3.2 and the advance element 3.3 and the rotating element 3.4 are each provided at their peripheral surface with a knurling or the like to prevent the fingers from slipping off.

In the illustrated example the pitch of the first screwthread 5 and the second counterpart screwthread 7 which is in engagement therewith is so selected that the swab carrier 1 can be moved from its first longitudinal position into its second longitudinal position by a single revolution of the advance element 3.3 of the actuating grip 3.1 about the longitudinal axis 1.3 relative to the grip device 3.2 and thus relative to the casing tube 2. In order to prevent the advance element 3.3 tilting relative to the grip device 3.2 when the screwthread pitch is so comparatively high and thus to ensure longitudinal displacement of the swab carrier 1 relative to the casing tube 2 as easily and as trouble-free as possible, the first screwthread 5 and the second counterpart screwthread 7 are of a multi-flight nature.

In the illustrated embodiment the swab carrier 1 comprises a distal carrier portion 10 and a tubular proximal carrier portion 11, which are releasably connected together by way of an elongate coupling portion 12. The coupling portion 12 is introduced into the interior of the proximal carrier portion 11 and extends in the distal direction into a first opening 13 in the distal carrier portion 10.

In this case the coupling portion 12 comprises a metal wire which is wound in a spiral configuration at the distal end of the coupling portion. In this case the distal part of the winding forms the distal locking part 14 of the coupling portion 12 while the proximal part of the winding forms the proximal locking part 15 of the coupling portion 12. The distal locking part 14 is fitted in the first opening 13 of the distal carrier portion 10, which is delimited by a cylindrical first wall part 16. The proximal locking part 15 is fitted in the cavity in the interior of the proximal carrier portion 11 which is delimited by a second wall part 17 which is also cylindrical.

The wall of the coupling portion 12 which forms the locking parts 14 and 15 is of a resilient nature transversely with respect to the longitudinal direction of the coupling portion 12. In this case in the relaxed condition, that is to say the condition of not being introduced into the carrier portions 10 and 11, the winding transversely with respect to its longitudinal direction involves an oversize in relation to the first and second wall parts 16 and 17 respectively. Consequently the distal locking part 14 bears under a bias against the first wall part 16 and the proximal locking part 15 bears under a bias against the second wall part 17.

The locking parts 14 and 15, by virtue of that biasing effect, cooperate with the wall parts 16 and 17 respectively in the manner of a frictional locking connection which is releasable in the axial direction of the coupling portion 12. In this case the distal locking part 14 co-operates inter alia lockingly in the distal direction with the first wall part 16 of the distal carrier portion 10 and the proximal locking part 15 co-operates lockingly in the proximal direction with a second wall part 17 of the proximal carrier portion 11. In that way the two carrier portions 10 and 11 which bear against each other in the region of the join 18 are fixed relative to each in their longitudinal direction.

The force required to release the connection between the carrier portions 10 and 11 is substantially determined in accordance with the biasing force with which the locking parts 14 and 15 bear against the wall parts 16 and 17 respectively. That biasing effect is in turn determined in accordance with the amount by which the winding of the coupling portion 12 is deformed in its inserted condition, in relation to its relieved condition, and accordingly therefore the oversize which the winding has in its relieved condition, in relation to the diameter of the wall parts 16 and 17.

The fact that the two wall parts 16 and 17 each extend as far as the join 18 and the two locking parts 14 and 15 directly adjoin each other ensures moreover that the two carrier portions 10 and 11 are fixed transversely with respect to their longitudinal direction. The two carrier portions 10 and 11 are thereby fixed in their aligned position in a simple manner without further guide means or the like being required for that purpose.

The coupling portion 12 projects in the proximal direction out of the proximal carrier portion 11 which is carried in the actuating grip 3.1. Arranged at that end is a grip device 19 at which the coupling portion 12 can be gripped and, with a counterpart hold for example at the actuating grip 3.1, can be pulled in the proximal direction out of its seat in the first opening 13 in the distal carrier portion 10. That then releases the connection between the two carrier portions 10 and 11.

The first and second wall parts 16 and 17 are each of the same diameter. As a result the pulling force required for pulling the distal locking part 14 out of its seat in the distal carrier portion remains substantially constant over the entire release procedure. That contributes to a uniform jerk-free release movement, whereby it is easier to hold the distal end of the device over a transportation vessel for the swab carrying the smear.

It will be appreciated that the connection between the carrier portions may also be of a different form in other variants of the device according to the invention. Thus it is possible for example to provide locking parts which are separate from each other. They can also act in different ways. Thus, for example one or both locking parts may act in the manner of a positively locking connection. The association wall parts then only have to have corresponding undercut configurations, in relation to the direction of rotation, into which correspondingly resilient projections of the respective locking part then releasably engage.

Provided at the exit of the coupling portion 12 at the proximal end of the actuating grip 3.1 is a securing means 20 to prevent the distal end of the coupling portion 12 from being unintentionally pulled out of its seat in the first opening 13. The securing means comprises an adhesive point 20 consisting of a hardening plastic material which is fixedly joined both to the material of the coupling portion 12 and also the material of the actuating grip 3.1. The securing means 20 is destroyed to pull the distal end of the coupling portion 12 out of the first opening 13, for example by being released from the actuating grip 3.1 by a shearing movement transversely with respect to the longitudinal axis of the device. It can however also be destroyed and thus released by applying a correspondingly high level of pulling force on the coupling portion.

It will be appreciated that in other embodiments of the invention the securing means can also take over the function of locking the coupling portion with respect to one of the carrier portions. Thus it is possible for example that the above-described adhesive point is arranged in the distal end of the internal cavity of the proximal carrier portion and fixes the coupling portion there, without the provision of a further proximal locking part.

Figure 1A:
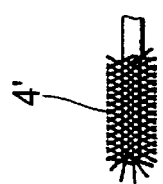
FIG. 1a shows a side view of an alternative embodiment of the swab in the form of a brush, in the device illustrated in FIG. 1.

FIG. 1*a* is a side view of a brush 4' which can be arranged alternatively to use of the swab 4 at the distal end 1.1 of the swab carrier 1. In its distal end portion the brush 4' has radially outwardly extending bristles of nylon.

Figure 2:
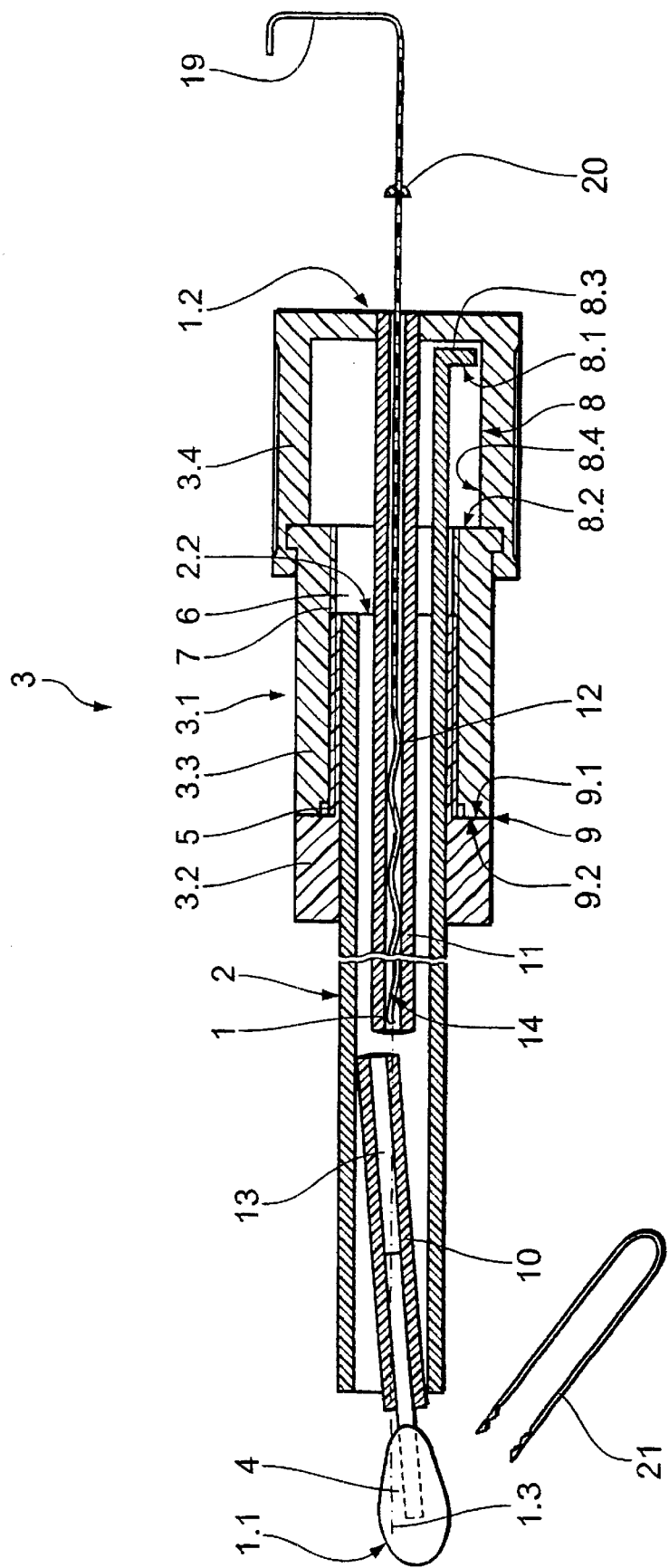
FIG. 2 is a view in section through the embodiment of FIG. 1 with the detached distal carrier portion in a first condition.

FIG. 2 shows the device of FIG. 1 in a condition in which the distal locking part 14 of the coupling portion 12 has been pulled in the proximal direction out of the seat in the first opening 13 of the distal carrier portion 10 and is now arranged in the interior of the proximal carrier portion 11.

In that condition the connection between the distal carrier portion 10 and the proximal carrier portion 11 is released. In that condition the distal carrier portion 10 carrying the swab 4 can be easily released from the casing tube 2. In the illustrated embodiment the inside diameter of the casing tube 2 for that purpose involves an oversize with respect to the outside diameter of the swab carrier 1. When the casing tube 2 is suitably inclined with respect to the horizontal the distal carrier portion 10 which has been separated off is released from the casing tube 2.

It is sufficient here for example for the distal end of the device to be positioned perpendicularly above the opening of the filled transportation vessel and for the distal carrier portion 10 to be separated off in the manner described above. The separated-off carrier portion 10 on which the swab 4 with the smear is disposed is then released from the casing tube 2 as a result of the action of the force of gravity and slides into the transportation fluid. In this case therefore the separated-off swab 4 with the sample which is to be later analyzed passes into the transportation vessel, without coming into contact with possible sources of contamination.

In the illustrated example the distal carrier portion 10 is separated off, with the swab carrier 1 in the second longitudinal position. It will be appreciated however that the distal carrier portion 10 can also be separated off in any other longitudinal position of the swab carrier 1. In particular, that is also possible with the swab carrier 1 in the first longitudinal position in which the swab 4 is disposed entirely in the casing tube 2 and is thus protected thereby from contamination.

Figure 3:
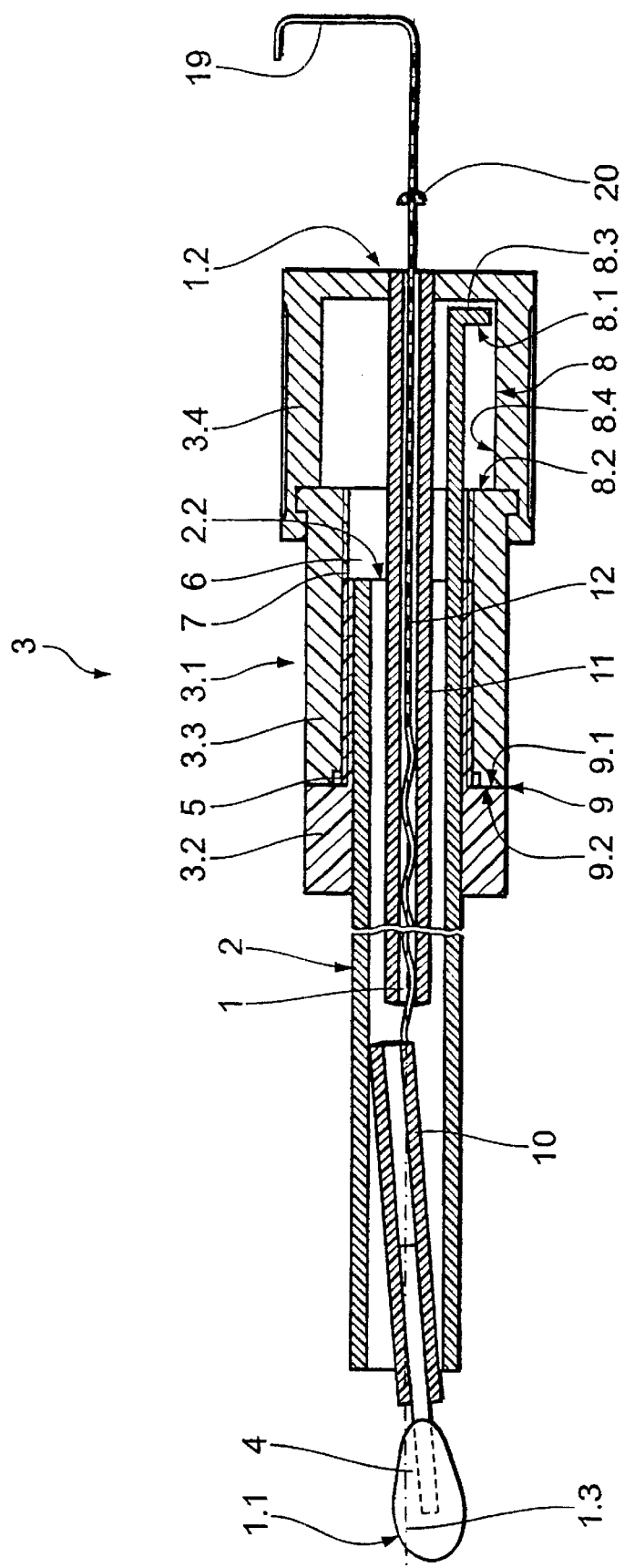
FIG. 3 is a view in section through the embodiment of FIG. 1 with the detached distal carrier portion in a second condition.

As indicated in FIG. 3 the coupling portion 12 can in addition again be displaced in the distal direction and used to push the separated-off carrier portion 10 out of the casing tube 2 in the event of tilting or sticking in the casing tube 2, or at least to assist in releasing it from the casing tube 2. In that respect the securing means 20 can additionally also be released from the coupling portion 12 so that the coupling portion 12 can be displaced as far as possible in the distal direction.

In the illustrated example the distal carrier portion 10 is of a length of about 5 cm so that the device is suitable for use in conjunction with the transportation containers which are usual at the present time.

In the illustrated example the swab carrier 1, the casing tube 2 and the displacement device 3 comprise biocompatible plastic materials and the coupling portion comprises a biocompatible metal. The actuating grip 3.1 and the grip element 3.2 involve injection moldings. The swab 4 comprises calcium alginate wadding with which unfalsified investigation results can be particularly well achieved.

Figure 4:
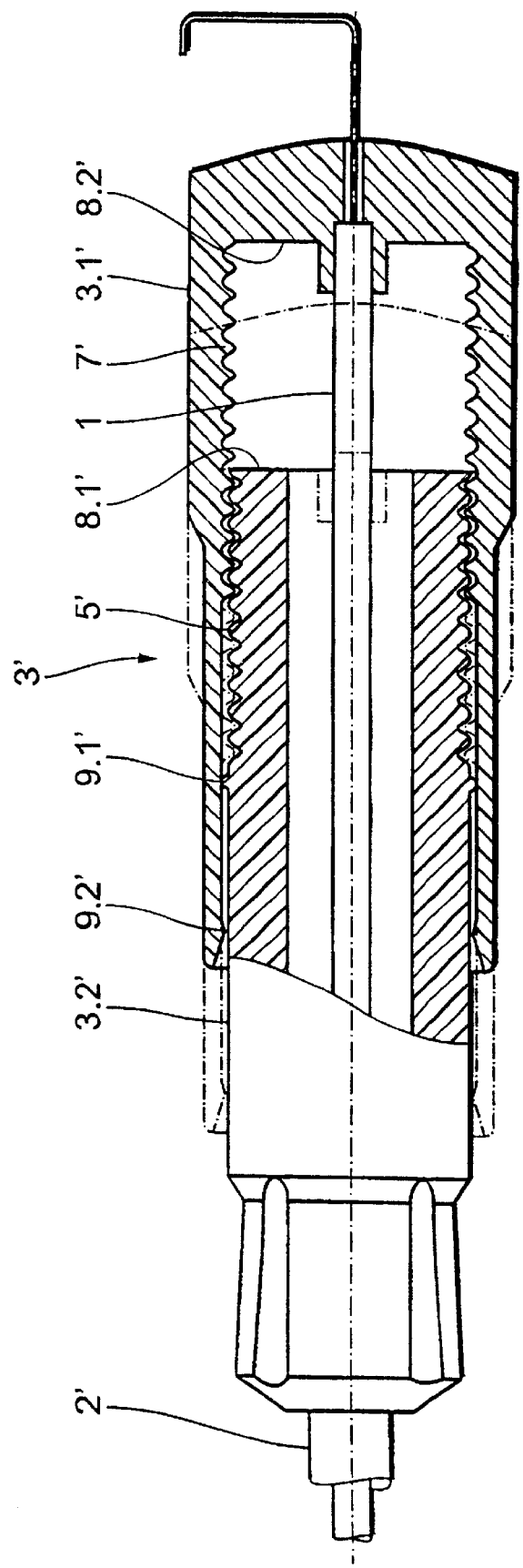
FIG. 4 shows a detail section through another preferred embodiment of the device according to the invention.

FIG. 4 is a view in section through the proximal end of a further embodiment of the invention which substantially corresponds to the embodiment shown in FIG. 1 so that here only the differences in relation to the FIG. 1 structure will be discussed. The difference in relation to the FIG. 1 embodiment is that the displacement device 3' is made from plastic parts carrying a screwthread. In this arrangement the actuating grip 3.1' which is made in one piece and the grip element 3.2' each acquire their definitive shape for use thereof, in an injection procedure. In particular, the first screwthread 5' and the third abutment surface 9.1' as well as the second screwthread 7' and the second and fourth abutment surfaces 8.2' and 9.2' directly acquire their final shape in the respective working operation. That affords on the one hand particularly fast and simple manufacture of the device and also provides a device which is particularly light and thus convenient and comfortable to handle by virtue of the components being low in weight, with good stability.

It is also worth noting in relation to this embodiment that the outer actuating grip 3.1' is "non-losably" latched on the inner grip element 3.2' because an annular abutment surface 9.1' is provided on the grip element 3.2' which is connected to the sleeve. It interacts with an annular abutment surface 9.2' when the grip element 3.2' comes free from the screwthread. That forms a blocking means to prevent the actuating grip 3.1' from being pulled off the grip element 3.2' when the latter is completely unscrewed from the screwthread. The actuating grip can then be idly rotated and can only be pulled off with a gentle jerk, in which case the edge of the abutment surface 9.2' has to overcome the further abutment surface 9.1' which forms a threshold. That can be effected only be applying force, with elastic deformation of the two grip components.

The invention is not limited in respect of implementation thereof to the preferred embodiments set forth by way of example hereinbefore. On the contrary, a number of variants are possible, which make use of the illustrated structure, even in design configurations of a basically different nature.

Thus, in a variant of the invention—as shown in FIG. 2—the swab carrier 13 can also be removed from the casing tube 2 by a pair of tweezers 21. The tweezers can be enclosed with the device, in which case, in an embodiment (not shown) a suitable receiving means for the tweezers 21 in the form of a clamping holder is provided on the casing tube 2 or on the grip element 3.

What is claimed is:

1. A device for taking a biological or cytological smear from the human or animal body comprising a casing tube in which there is longitudinally movably arranged a swab carrier whose distal end is provided with a swab, and a displacement device which is arranged at the proximal end of the device and which further comprises a grip element arranged at the proximal end of the casing tube and an actuating grip connected to the proximal end of the swab carrier and by the actuation of which the swab carrier is movable relative to the casing tube at least between a first longitudinal position in which the swab is disposed entirely in the interior of the casing tube and a second longitudinal position in which the swab projects at least in part out of the distal end of the casing tube to receive the smear, wherein the swab carrier comprises at least distal and proximal carrier portions, which are releasably connected together by way of a coupling portion characterized in that the coupling portion (12) is introduced into the proximal carrier portion which is of a tubular configuration, wherein it extends in the proximal direction through the actuating grip and in the distal direction into a first axial opening at the proximal end of the distal carrier portion, and wherein the coupling portion locks the carrier portions relative to each other in their longitudinal direction by a positively locking, frictional locking and/or adhesive connection to the distal carrier portion and to the proximal carrier portion and/or the actuating grip in such a way that the connection thereof is releasable by pulling the distal end of the coupling portion in the proximal direction out of the first axial opening.

2. The device as set forth in claim 1 wherein the coupling portion has at least one distal locking part and at least one proximal locking part, wherein the distal locking part co-operates lockingly in the distal direction and releasably with a first wall part of the distal carrier portion and the proximal locking part co-operates lockingly in the proximal direction and releasably with a second wall part of the proximal carrier portion or the actuating grip.

3. The device as set forth in claim 2 wherein the connection between the distal locking part and the distal carrier portion or the connection between the proximal locking part and the proximal carrier portion or the actuating grip in the manner of a frictional locking connection which is releasable in the axial direction of the coupling portion.

4. The device as set forth in claim 3 wherein the distal and proximal locking parts each have at least in portion-wise manner transversely with respect to its longitudinal direction an oversize relative to the first or second wall part respectively, to produce the releasable frictional locking connection.

5. The device as set forth in claim 2, wherein at least one of the distal or proximal locking parts respectively is resilient transversely with respect to its longitudinal direction and bears under a biasing effect against the respective wall part.

6. The device as set forth in claim 5 wherein at least one of the first or second wall parts respectively is of a substantially cylindrical configuration and the respective locking part is formed by a spiral-shaped part.

7. The device as set forth in claim 6 wherein the proximal carrier portion is of inside dimensions which substantially correspond to the inside dimensions of the first axial opening at the distal end of the carrier portion to receive the distal end of the coupling portion which is pulled out the first axial opening.

8. The device of claim 7 wherein at its proximal end the coupling portion has a grip device for pulling its distal end in the proximal direction out of the first axial opening.

9. The device of claim 8 wherein at least one means for securing is provided to prevent the distal end of the coupling portion from being unintentionally pulled out of the first axial opening.

10. The device as set forth in claim 9 wherein the securing means is destroyed when the distal end of the coupling portion is pulled out of the first axial opening.

11. The device of claim 10 wherein the securing means forms the locking means for locking the coupling portion in the distal carrier portion or in the proximal carrier portion or the actuating grip respectively.

12. The device of claim 11 wherein the coupling portion and the proximal and distal carrier portions are configured so that the carrier portions are fixed by the coupling portion transversely with respect to their longitudinal direction in a position of being substantially aligned in their longitudinal direction.

13. The device of claim 12 wherein the inside dimensions of the casing tube and the outside dimensions of the swab carrier or the swab have a difference between them such that the distal carrier portion, after release of the connection to the proximal carrier portion, is released from the casing tube by virtue of the action of the force of gravity when the casing tube is suitably inclined relative to the horizontal and/or by the action of weak inertia forces.

14. The device as set forth in claim 13 wherein the inside dimensions of the casing tube in the distal end region adjoining the distal carrier portion have a slight oversize relative to the outside dimensions of the distal carrier portion or the swab respectively.

15. The device of claim 14 wherein the length of the distal carrier portion is at least 1 cm and less than 10 cm.

16. The device of claim 15 wherein the swab carrier, the casing tube and the displacement device are such that the swab carrier is rotatable about the longitudinal axis at least in its second longitudinal position relative to the casing tube.

17. The device as set forth in claim 16 wherein the actuating grip further comprises an advance device and a rotating device which is fixedly connected to the proximal end of the swab carrier, and at least one of the rotating device or the swab carrier is arranged on the advance device rotatably about the longitudinal axis relative to the advance device.

18. The device of claim 17 wherein at least one of the swab carrier, or the casing tube or the displacement device is such that the longitudinal mobility of the swab carrier relative to the casing tube is limited to a longitudinal movement between its first and second longitudinal positions by a proximal abutment device and a distal abutment device.

19. The device of claim 18 wherein the displacement device is designed in the manner of a screw drive which produces an advance movement in the longitudinal direction of the device.

20. The device as set forth in claim 19 wherein the casing tube and the swab carrier are rotatable relative to each about the longitudinal axis and the displacement device includes a first screwthread which is arranged on the casing tube and which to produce a longitudinal movement of the swab carrier relative to the casing tube upon rotation of the actuating grip relative to the casing tube about the longitudinal axis is in engagement with a second counterpart screwthread provided on the swab carrier or on the actuating grip.

21. The device as set forth in claim 20 wherein the first screwthread is arranged at the outside periphery of the proximal end of the casing tube and the actuating grip is designed in the manner of a screw cap, wherein the swab carrier is passed through an orifice coaxial therewith at the distal end of the actuating grip and the second counterpart screwthread is arranged at the distal end of the actuating grip (3.1; 3.1') at the inside periphery of the orifice.

22. The device as set forth in claim 20 wherein each of the first and second screwthreads has a pitch so is that the movement of the swab carrier between its first longitudinal position and its second longitudinal position is produced by substantially one revolution of the actuating grip relative to the casing tube.

23. The device of claim 22 wherein the first screwthread and the second counterpart screwthread are of a multi-flight nature.

24. The device of claim 23 wherein the casing tube and the swab carrier respectively comprise biocompatible plastic material and the coupling portion comprises biocompatible plastic material or metal.

25. The device of claim 24 wherein at least one of the actuating grip or the grip element have a plastic material body produced by means of an injection molding or blow molding process.

26. The device of claim 25 wherein the actuating grip is latched on the inner grip element through an annular abutment surface on the grip element connected to the sleeve, which abutment surface interacts with an annular abutment surface when the grip element comes free from the screwthread.

27. The device of claim 26 wherein the swab comprises calcium alginate.

28. The device of claim 27 wherein a pair of tweezers is provided to remove the swab carrier.

29. The device of claim 26 wherein the swab comprises a cotton-aluminum mixture.

30. The device of claim 26 wherein the swab is formed by a nylon brush.

31. The device of claim 28 wherein the pair of tweezers is releasably connectable to the device for storage purposes.

32. A device for taking a biological or cytological smear from the human or animal body comprising:

a casing tube in which there is longitudinally movably arranged a swab carrier whose distal end is provided with a swab, and a displacement device at the proximal end of the device and which includes a grip element at the proximal end of the casing tube and an actuating grip connected to the proximal end of the swab carrier, the actuation of the actuating grip moving the swab carrier relative to the casing tube at least from a first longitudinal position in which the swab is disposed entirely in the interior of the casing tube into a second longitudinal position in which the swab projects at least in part out of the casing tube distal end to receive the smear, or vice-versa;

the swab carrier comprising at least a distal carrier portion and a proximal carrier portion, which are releasably connected together by way of a coupling portion such that the coupling portion is introduced into the proximal carrier portion which is of a tubular configuration, wherein it extends in the proximal direction through the actuating grip and in the distal direction into a first axial opening at the proximal end of the distal carrier portion, and wherein the coupling portion locks the respective carrier portions relative to each other in their longitudinal direction by a positively locking, frictional locking and/or adhesive connection to the distal carrier portion and to the proximal carrier portion and/or the actuating grip so that the connection thereof is releasable by pulling the distal end of the coupling portion in the proximal direction out of the first axial opening;

the coupling portion further comprising at least one distal locking part and at least one proximal locking part, wherein the distal locking part co-operates lockingly in the distal direction and releasably with a first wall part of the distal carrier portion and the proximal locking part co-operates lockingly in the proximal direction and releasably with a second wall part of the proximal carrier portion or the actuating grip;

the connection between the distal locking part and the distal carrier portion or the connection between the proximal locking part and the proximal carrier portion or the actuating grip being a frictional locking connection which is releasable in the axial direction of the coupling portion;

the distal and proximal locking parts each having at least in portion-wise manner transversely with respect to its longitudinal direction an oversize relative to the first or second wall part respectively, to produce the releasable frictional locking connection;

at least one of the distal and proximal locking parts being resilient transversely with respect to its longitudinal direction and bearing under a biasing effect against the respective wall part;

at least one of the first and second wall parts being of a cylindrical configuration and the respective locking part being formed by a spiral-shaped part;

the proximal carrier portion being of inside dimensions which correspond to the inside dimensions of the first axial opening at the carrier portion distal end to receive the coupling portion distal end which is pulled out the first axial opening;

the coupling portion having a grip device at its proximal end for pulling its distal end in the proximal direction out of the first axial opening;

at least one means for securing being provided to prevent the coupling portion distal end from being unintentionally pulled out of the first axial opening;

the at least one securing means being destroyed when the coupling portion distal end is pulled out of the first axial opening;

the at least one securing means forming the locking means for locking the coupling portion in the distal carrier portion or in the proximal carrier portion or the actuating grip;

the coupling portion and the proximal and distal carrier portions being configured so that the respective carrier portions are transversely fixed by the coupling portion with respect to their longitudinal direction in a position of being substantially aligned in their longitudinal direction;

the casing tube inside dimensions and the outside dimensions of the swab carrier or the swab having a difference between them such that the distal carrier portion, after release of the connection to the proximal carrier portion, is released from the casing tube by virtue of the action of the force of gravity when the casing tube is suitably inclined relative to the horizontal and/or by the action of weak inertia forces;

the casing tube inside dimensions in the distal end region adjoining the distal carrier portion having a slight oversize relative to the outside dimensions of the distal carrier portion or the swab, respectively;

the length of the distal carrier portion being at least 1 cm and less than 10 cm;

the swab carrier, the casing tube and the displacement device being such that the swab carrier is rotatable about the longitudinal axis at least in its second longitudinal position relative to the casing tube;

the actuating grip further comprising an advance device and a rotating device which is fixedly connected to the swab carrier proximal end, and at least one of the rotating device and the swab carrier being arranged on the advance device rotatably about the longitudinal axis relative to the advance device;

at least one of the swab carrier, the casing tube and the displacement device being such that the swab carrier is limited relative to the casing tube to a longitudinal movement between its first and second longitudinal positions by a proximal abutment device and a distal abutment device;

the displacement device being a screw drive which produces an advance movement in the longitudinal direction of the device;

the casing tube and the swab carrier being rotatable relative to each about the longitudinal axis, with the displacement device comprising a first screwthread on the casing tube to produce a longitudinal movement of the swab carrier relative to the casing tube upon rotation of the actuating grip relative to the casing tube about the longitudinal axis, the first screwthread being in engagement with a second counterpart screwthread provided on the swab carrier or on the actuating grip;

the first screwthread being at the outside periphery of the proximal end of the casing tube with the actuating grip being a screw cap, wherein the swab carrier is passed through an orifice coaxial therewith at the actuating grip distal end and the second counterpart screwthread being at the actuating grip distal end at the inside periphery of the orifice;

each of the first and second screwthreads having a pitch selected such that the movement of the swab carrier between the first and second longitudinal positions is produced by substantially one revolution of the actuating grip relative to the casing tube;

each of the first and second screwthreads being of a multi-flight nature;

the casing tube and the swab carrier respectively comprising biocompatible plastic material;

the coupling portion comprising biocompatible plastic material or metal;

at least one of the actuating grip and the grip element having a plastic material body produced by an injection molding or blow molding process;

the actuating grip being latched on the inner grip element through an annular abutment surface on the grip element connected to the sleeve, which abutment surface interacts with an annular abutment surface when the grip element comes free from the screwthread; and the swab comprising calcium alginate.

* * * * *